(12) United States Patent
Fotinos

(10) Patent No.: US 6,346,255 B1
(45) Date of Patent: Feb. 12, 2002

(54) PLANT POLAR LIPID PERMEATION ENHANCER IN A COSMETIC PAD FOR IMPROVING SKIN APPEARANCE

(75) Inventor: Spiros Fotinos, Athens (GR)

(73) Assignee: Lavipharm Laboratories Inc., East Windsor, NJ (US)

( * ) Notice: Subject to any disclaimer, the term of this patent is extended or adjusted under 35 U.S.C. 154(b) by 0 days.

(21) Appl. No.: 09/232,422

(22) Filed: Jan. 15, 1999

Related U.S. Application Data

(60) Provisional application No. 60/071,379, filed on Jan. 15, 1998, provisional application No. 60/075,890, filed on Feb. 25, 1998, provisional application No. 60/087,917, filed on Jun. 4, 1998, and provisional application No. 60/095,089, filed on Aug. 3, 1998.

(51) Int. Cl.[7] ............................ A61K 6/00; A61F 13/00; A61F 13/02; A01N 25/34
(52) U.S. Cl. ...................... 424/401; 424/402; 424/448; 424/449
(58) Field of Search ................................ 424/402, 401, 424/78.03, 443, 448, 449

(56) References Cited

U.S. PATENT DOCUMENTS 5,968,533 A * 10/1999 Porter et al. ................. 424/401
6,087,341 A * 10/1999 Khavari et al. ............... 514/44

* cited by examiner

Primary Examiner—Thurman K Page
Assistant Examiner—S. Howard
(74) Attorney, Agent, or Firm—Dechert; Thomas S. Deibert

(57) ABSTRACT

Devices for the improvement of skin appearance are provided, said devices including a pad with a backing layer, a release layer, and a vehicle located therebetween, the vehicle containing a cosmetic formulation and a skin permeation enhancer, wherein the skin permeation enhancer includes a plant polar lipid. The invention also relates to a method of improving skin appearance using the devices of the invention.

20 Claims, 1 Drawing Sheet

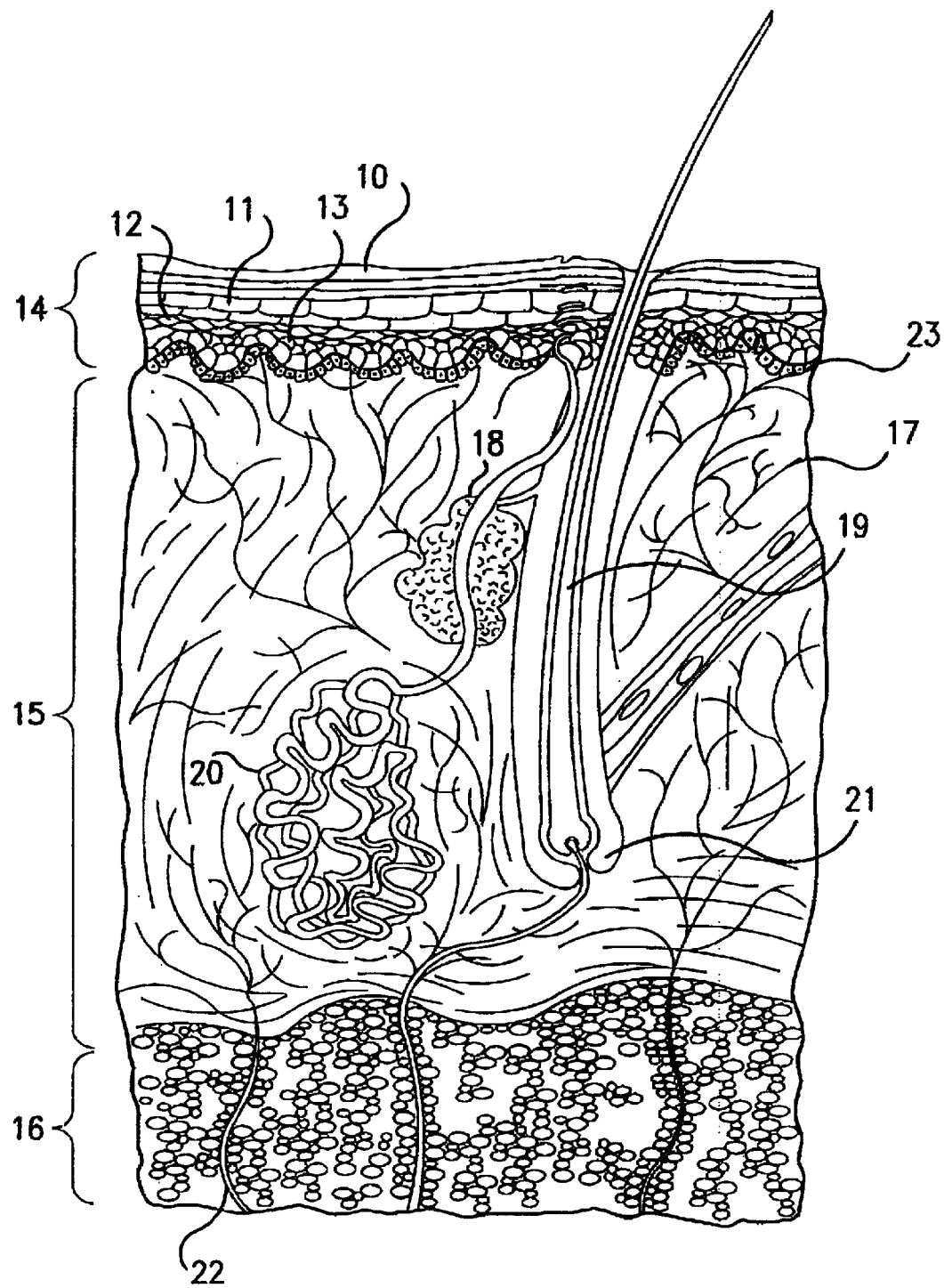
FIG I

PLANT POLAR LIPID PERMEATION ENHANCER IN A COSMETIC PAD FOR IMPROVING SKIN APPEARANCE

CROSS REFERENCE

This invention claims priority from Provisional Application, Serial No. 60/071,379, filed Jan. 15, 1998; Provisional Application, Serial No. 60/075,890 filed Feb. 25, 1998; Provisional Application, Serial No. 60/087,917 filed Jun. 4, 1998; Provisional Application, Serial No. 60/095,089, filed Aug. 3, 1998, the provisional applications being herein incorporated by reference.

TECHNICAL FIELD

The present invention concerns methods and compositions for the improvement of skin appearance by topical application of a cosmetic formulation in the form of a pad, which contains a skin permeation enhancer consisting of a plant polar lipid.

BACKGROUND OF THE INVENTION

Skin forms a barrier between the internal organs of the body and the environment. The condition of the skin reflect the health and youthfulness of the individual. Consequently, it is desirable to enhance these skin properties particularly in aging individuals. Active agents have been identified that have some beneficial effect on skin when applied as a cream or ointment although this beneficial effect is limited by the ability of the active agent to penetrate through the stratum corneum of the epidermis to the basal cells below. The epidermis of the skin has a thickness of about 0.1 mm with a layer of keratinized cells at the surface and a basal layer that continually produces new cells in a cycle of cell growth and cell death. (FIG. 1). It is desirable to develop a cosmetic formulation, which when applied to the surface of the skin, provides increased penetration of active ingredients to the basal layer. To improve skin penetration of topically administered agents, synthetic chemical substances have been added to the cosmetic formulations as penetration enhancers such as alcohols, polyalcohols and various surfacatants. These chemicals have some efficacy although they may be accompanied by undesirable side effects such as skin irritation or an immune reaction. There is therefore a need for enhancers which are capable of improving the penetration of active agents to the basal layer of the skin without causing an immune response or unpleasant irritation.

Although cosmetics are commonly delivered to the target site in the form of a cream or ointment, patch-type delivery systems have been developed for topical delivery of cosmetics. Typically, these patches include an adhesive layer, multiple polymer layers containing reagents and a backing layer. EP 0410921 A2 describes a dressing for transcutaneous application of active substances for both therapeutic and cosmetic purposes which has five layers, but apparently lacks enhancers. The reference describes the use of these dressings for the delivery of any cosmetic or therapeutic active agent of vegetable, chemical, pharmacological and biological origin. In contrast, GB 2 265 086 is directed specifically to topical administration of skin whitening agents where a three or five layer system contains active agent, enhancers, and stabilizers in the adhesive layer. In this system, the release and absorption of the active ingredients through the skin was achieved by utilizing high concentrations of permeation enhancers. Indeed, the concentration of permeation enhancer used in this reference was as much as sixfold that of the active agent.

Other skin cosmetic compositions in the form of patches are disclosed in WO 96/14822 and the corresponding U.S. Pat. No. 5,784,978 for improving the appearance of skin. This reference utilizes ascorbic acid as the active agent in optional combination with moisturizers contained in a patch analogous to a transdermal patch. The reference lists a number of compounds for use as penetration enhancers in transdermal patches as used for systemic delivery citing Pfister and Hseih (1990) Pharmaceutical Technology, September 1990 and October 1990.

There is a need for a cosmetic patch or pad that is directed to topical delivery of active agent rather than systemic delivery and provides enhanced penetration of active agents to the basal layer of the skin. The enhancer should possess desirable physicochemical properties, with minimum undesirable skin reactions, while at the same time being cost effective and readily manufactured. A benefit of such an enhancer would be to reduce the concentration of active ingredients without reducing the overall effectiveness of the patch.

SUMMARY

This invention satisfies the above needs. A novel device for improving skin appearance is provided. In preferred embodiments of the invention, a device for the improvement of skin appearance is provided that includes a pad having a backing layer, a vehicle and a release layer, the vehicle being located therebetween, the vehicle including a cosmetic formulation and a skin permeation enhancer, wherein the skin permeation enhancer includes a plant polar lipid. The plant polar lipid can be for example, a phospholipid or a glycolipid. More particularly, the plant polar lipid may include a ceramide preparation including at least one of a ceramide and a glycoceramide. In an embodiment of the invention, the ceramide preparation contains at least 50% ceramide and glycoceramide, more particularly, the enhancer is present in a range of 0.1%–5% w/w of the cosmetic formulation. In a preferred embodiment, the permeation enhancer is formulated in the absence of a synthetic lipid and in the absence of a surfactant.

The cosmetic formulation may further include a cosmetic active agent and at least one of an antimicrobial agent, an antioxidant, a preservative, an anti-irritant, a plasticizer and a solubilizer such that the concentration range of the cosmetic active agent may be in the range of 1 to 20% w/w, the anti-microbial agent in the range of 0 to 5% w/w, the anti-oxidant is 0 to 4% w/w, the preservative in the range of 0 to 5% w/w, the anti-irritant in the range of 0 to 7% w/w, the plasticizer in the range of 0–10% w/w, and the solubilizer in the range of 0 to 5% w/w. Examples of cosmetic agent for incorporation into the device include anti-hyperpigmentation agents, anti-blotching agents, anti-aging agents, eye contour agents, slimming agents, anti-cellulite agents, soothing agents, sunburn agents, anti-irritating agents, skin firming agents, anti-elastase agents, anti-collagenase substances, free radical scavengers, seboregulators, hydratives, and AHA (α-hydroxy acid) agents, vitamins, anti-oxidants, anti-irritants and minerals.

In a further embodiment of the invention, a method is provided for delivering a cosmetic agent to a topical target site for improving skin appearance, that includes (a) selecting a multilaminate device including a backing layer, a vehicle and a release liner; (b) providing the cosmetic agent and an enhancer for dispersion within the vehicle wherein the enhancer is a plant polar lipid including a sphingolipid, more particularly a ceramide preparation; and (c) forming a device for improvement of skin appearance.

In a further embodiment of the invention, the cosmetic agent for improving skin appearance may be selected so as to achieve any of the following: increased skin elasticity, decreased wrinkles, removal of pimples, reduction in cellulitis, increased skin moisture, regulation of sebum secretion, reduced hyperpigmentation and blotching.

BRIEF DESCRIPTION OF THE FIGURES

FIG. 1 shows a diagrammatic representation of a skin cross section to illustrate the extent of penetration of the active agent to the basal layer in a topical administration versus a penetration to the capillaries in the dermis of an agent in a systemic administration. (10) stratum corneum, (11) Stratum lucidum, (12) stratum spinosum, (13) stratum gerninativum, (14) epidermis, (15) dermis, (16) hypodermis, (17) capillary network, (18) sebaceous gland, (19) hair shaft, (20) apocrine sweat gland, (21) hair follicle, (22) blood vessel, (23) basal layer.

DETAILED DESCRIPTION OF THE INVENTION

The present invention is directed to a device for improving skin appearance that relies on topical administration of an active agent to a target site in the presence of a skin enhancer, where the skin enhancer directs the active agent through the stratum corneum thereby increasing the effectiveness of the active agent.

The term "target site" used here and in the claims is defined as the area of the skin which is characterized by coarseness, wrinkling, telangiectasia, discrete hyperpigmented and hypo-pigmented macules and atrophy.

The term "active agents" used here and in the claims is defined as cosmetics that are known in the art which can be used alone or in combination in the compositions of the proposed formulations.

The term "other additives" used here and in the claims is defined as ingredients such as stabilizers, solubilizers, anti-irritants, anti-oxidants and plasticizers, anti-microbials and preservatives which can improve the efficacy and the mechanical properties of the formulation.

The term "topical application" used here and in the claims is defined as a formulation which is in contact with the outermost layer of the skin through an adhesive layer.

The term "pad" or "patch" used here interchangeably and in the claims is defined as a device that includes a backing layer, a vehicle containing the active agents and other additives and a release liner where the backing layer is located on one side of the vehicle and the release liner is located in the other side of the vehicle, and the pad may be fixed to the skin following removal of the release liner.

The term "cosmetic pad" or "cosmetic patch" used here and in the claims is defined as a pad that is applied to the external part of the human body (epidermis, face, neck, hand, thigh, etc.) for changing the appearance by protecting or keeping the skin in good condition (EEC Directive 76/1768, August 1993, for Cosmetics).

The term "safe and effective" used here and in the claims is defined as a formulation which can induce a positive modification to the skin while minimizing any undesirable effect. The term "vehicle" used here and in the claims is defined as a liquid or solid reservoir, the solid reservoir formed from a polymeric matrix.

Enhancers can be distinguished according to those that enhance skin penetration and membrane solubility which are fatty acid esters and fatty alcohol ethers and those that enhance permeation through the skin to the blood which are organic chemical solvents such as alcohols and dimethylsulfoxide U.S. Pat. No. 5,005,342.

According to preferred embodiments of the invention, a new class of permeation enhancer, namely plant polar lipids, that are similar to those found in sphingolipids in the membranes of cells, have been identified as permeation enhancers suitable for use in a multilaminate patch for topical administration of active agents so as to enhance their permeation into the skin. In an embodiment of the invention, plant polar lipids including glycolipids, phospholipids and sphingolipids are preferred to animal polar lipids because plant polar lipids are substantially non-immunogenic and non-irritant compared to neutral lipids and lipids of animal or synthetic origin. More particularly, plant polar lipids include ceramides and glycosylceramides. (Rieger, Cosmetics and Toiletries Magazine, 111 (1996) 33–45). These lipids are a component of the cell membrane of plants and are commonly extracted from wheat, rice, soya, millet and spinach. In a preferred embodiment of the invention, at least one of glycosylated or nonglycosylated plant ceramides are used as enhancers for the first time. In an embodiment of the invention, plant polar lipids may be obtained from angiosperms additional to those listed above and from gymnosperms and lower plants. Ceramide preparations from different plant sources may further be combined for use as an enhancer. Examples 1–41 utilize commercially available glycosylated ceramides from wheat having an aliphatic backbone between 15 and 20 carbons in length. However, it is also within the scope of the invention to utilize polar lipids having a aliphatic backbone of 10–25 carbons. In a preferred embodiment of the invention, a ceramide preparation is used which contains plant polar lipids (glycolipids, phospholipids, ceramides, glycoceramides) at 70–85%, proteins at 4–7%, apolar lipids at 5–15% and moisture at 1–3%. The percentage of ceramides and glycoceramides in a ceramide preparation used according to the invention may vary according to the source of the plant polar lipids and the method of purification. Preferably, the plant polar lipid composition in a ceramide preparation for use as an enhancer according to the invention is greater than 50%.

Plant polar lipids that are enriched in glycosyl ceramides may be purified according to the methods disclosed in FR-A-9106336; U.S. Pat. No. 5,466,782; and WO-A-92/21321. Commercial sources include Laboratories Serobiologiques, France; and Les Colorants Wackherr, France.

In embodiments of the invention, it is shown for the first time that plant polar lipids, more particularly at least one of a plant derived ceramide or a glycosylceramide at a concentration of greater than 50% in a plant lipid preparation, are effective enhancers for topical administration of cosmetic agents and can be used in the range of 0.1% to 5% w/w in a cosmetic preparation. This range is well below the range of concentrations of enhancers in the prior art. (WO 96/14822). Not only are the amounts of enhancer utilized according to embodiments of the invention relatively low but also these enhancers are biocompatible with normal skin so that problems of skin irritation can be avoided.

Animal derived ceramides have been used as active agents in topical lotions (EP 0542,549 A1 and WO 96/16635) and in patches U.S. Pat. No. 5,401,517. Animal derived glycosylated ceramides have been shown to be non-toxic moisturizing agents that also have anti-radical activity and an anti-elastase effect and hence have utility in treating aging skin. (Bizot-Foulon V. et al., Int. J. Cosmetic Science 11, 255–264, 1995). The present invention is directed to the novel use of plant polar lipids as enhancers to improve the penetration of active agents through the stratum corneum using a topically applied pad. Plant polar lipids have particular advantages over animal polar lipids because plant products have reduced incidence of skin irritation, immune response and have increased safety associated with absence of contamination of plant products by animal pathogens such as viruses and prions. These advantages are particularly important in a cosmetic pad because pads for topical delivery to the skin surface may be considerably larger in surface area than a transdermal patch for delivery of a pharmaceutical agent and may be applied for extended periods of time.

The cosmetic pad proposed in the present invention is designed in a variety of sizes and shapes dependent on the area of skin to be fitted. In particular, the shape of the cosmetic pad has been designed in such a way to comfortably accommodate the anatomical shape of the skin to be applied in preferred embodiments, the size of the cosmetic pad in the present invention can range from 0.5 to 200 cm$^2$.

In an embodiment of the invention, the cosmetic pad may be applied to a selected area of skin for a predetermined time ranging from 0.5 to 24 hours, preferably up to 8 hours and more preferably 4 hours per day. An intensive course of treatment may require at least a 3 month course of application for achieving a significant improvement in skin appearance.

The cosmetic pad includes a backing layer, a vehicle and an easily removable layer (release liner). The vehicle may be a polymeric matrix which acts as a solid reservoir for the active agents and other additives. Alternatively, the vehicle may be a liquid reservoir within a polymeric support. The cosmetic pad may be a multi-laminate pad. It may form a monolithic dosage unit.

The backing layer may be impermeable or occlusive but biocompatible to any substance retained by the vehicle. The backing layer may be made of any suitable material including plastic, fabric, woven or non-woven materials, cellophane, plastic films such as polyethylene, polyester, polyurethane, polyvinyl chloride and polyamide, and metallic foils. The backing layer can be composite, transparent, opaque, fleshtoned, aluminized or a combination of the foregoing, with thickness available with or without corona treatment and thickness from 1 to 5 mils (a mil is 1/1000 of an inch) and can be formed from any of CoTran™ 9720 (3M), Saranex®, DBLF-2015 (Dow Chemicals), Multilam fleshtoned polyester film 1009 (3M), or any other material recognized in the art as having the desired properties.

The vehicle is positioned adjacent to the backing layer of the cosmetic pad at one surface. Where the vehicle is a polymeric matrix solid reservoir, the thickness of the polymeric matrix can range from 1 to 15 mils, preferably from 3 to 10 mils, and more preferably 6 mils. The polymeric matrix can be made of synthetic adhesives such as acrylics, rubber, silicone, cellulose, or other suitable materials that may have pressure sensitive properties and adhere directly to the skin. The polymeric matrix can be made of inert materials which are further biologically and topically acceptable and compatible with the distributed active substances described below.

Preferably, topically acceptable polymers with adhesion properties may be acrylic based polymers such as the GELVA® series sold by Solvtia (Monsanto) and the DURO-TAK® series sold by National Starch, MA 31 Adhesive Research, Inc.; rubber-based polymers such as DURO-TAK® series sold by National Starch; and silicone-based polymers such as BIO-SPA X7-4302 SILICONE PSA sold by Dow Corning. The matrix can consist of at least one layer of adhesive polymeric polymer (for example: a polymer provided by Adhesive Research MA 31).

The polymer matrix is preferably formulated so that it exhibits pressure-sensitive adhesiveness at room temperature and possesses other desirable characteristics including good adherence to the skin, ability to be removed without injuring the skin tissue and retention of tackiness over the time of application.

Contained within the polymeric matrix is a plant polar lipid enhancer and a single agent or mixture of agents known in the art to be safe and effective for improving the skin appearance under specific conditions such as aging, photo damage and oxidative stress. Examples of such agents are listed below. In addition to the cosmetic agent and the plant polar lipid enhancer, the cosmetic formulation may further include anti-microbials, anti-oxidants, anti-irritants, solubilizers, and preservatives described in more detail below.

An easily removable layer or release liner may be positioned adjacent to the second surface of the vehicle, namely the exposed surface of the matrix and is removed prior to the application of the pad to the skin.

The removable layer can be made of materials impermeable to any substance dissolved in the vehicle layer, more specifically, it can be made of materials such as polyvinyl chloride, polyester, polyvinylidene chloride, natural high impact polystyrene, polyethylene, or paper.

Preferably the removable layer is made of natural, high impact polystyrene (grade code: 15623 or 15462) sold by REXAM Release or a siliconized polyester film sold also by REXAM Release. The thickness of the removable layer usually ranges from 3 to 10 mils, or may preferably be 10 mils.

In preferred embodiments of the present invention, cosmetic active agents known in the art may be incorporated in the polymeric matrix of the pad for improving skin appearance. These agents can be any of anti-hyperpigmentation, anti-blotching, anti-aging, eye contour, slimming, anti-cellulite, soothing/sunburn, anti-irritating, skin firming and lifting, anti-elastase and anti-collagenase substances, free radical scavengers, seboregulators, hydratives, vitamins and AHA ($\alpha$-hydroxy acids) products, anti-oxidants and minerals.

Anti-hyperpigmentation agents typically used for counterbalancing this condition can include tyrosinase inhibitors such as peptide mixtures and plant extracts, fermentation products, and antioxidants such as kojic acid, ascorbic acid derivatives, hydroquinone, synthetic or natural derivatives of hydroquinone and hydroquinone precursors. In a preferred embodiment of the invention, anti-hyper pigmentation agents are Melawhite of PENTAPHARM LTD, Switzerland; Biowhite™ of COLETICA, France; Etioline of SEDERMA, France; Arbossa of KELESIMA, Italy; Gatuline whitening of GATTEFOSSE, France; Ascorbocilan C of EXSYMOL, Monaco; and Kojic acid of ALPS PHARM., Japan. The cosmetic patches as presented in Examples 32 and 33 were further evaluated with regard to their hyperpigmentation activity. (See example 41)

Anti-blotching agents typically used for counterbalancing this condition can include saponines and caffeic acid containing plant extract and related compounds. Preferably in the present invention, anti-couprose agents include Gatuline A of GATTEFOSSE, France, and Ivy-Phytelenes of SEPEX, France. (see Examples 9–11)

Anti-aging agents include glycosaminoglycan derivatives such as chondroitin sulfate and ATP; other bioactivators such as farnesol and farnesol derivatives; panthenol and panthenol derivatives; beech tree bud extracts; and soya bean embryonic tissue extracts and related compounds. Preferably in the present invention, anti-aging agents are Unichodrin ATP and Unitrienol T-27, both of INDUCHEM Switzerland and Gatuline RC and Phyiderm® both of GATTEFOSSE, France.

Eye contour agents include natural and synthetic ingredients with anti-edematous and anti-inflammatory properties and related compounds. In a preferred embodiment of the invention, the eye contour agent includes Esculoside of COLETICA. (see Examples 12–16)

Slimming agents include xanthine base containing plant extracts, red seaweed extracts and the like. In a preferred embodiment of the invention, the slimming agents are selected from Phodysterone of SEGMA, France, and Slimmigen® (Liposome) of LABORATORIES SEROBIOLOGIQUES, France. (see Examples 21–23)

Anti-cellulite agents include bioactive polypeptides such as cytokines and related compounds. In a preferred embodiment of the invention, the anti-cellulite agent is MPC (Milk Peptide Complex) of CHEMISCHES LAB, Germany.

Soothing/sunburn anti-irritating agents include extracts of plants, red algae and inactivated bacterial cultures. In a preferred embodiment of the invention, soothing/sunburn anti-irritating agents are Repair Complex CLR, and Sedaplant Richter, both of CHEMISCHES LAB., Germany, and Phycosil of EXSYMOL, Monaco.

Skin firming and lifting agents include a mixture of plant protein fractions, flavonoids and tannins such as Gatuling Lifting of GATTEFOSSE, France. (see Example 17)

Anti-elastase and anti-collagenase agents include various lipoamino acids such as acylation products of palmitic acid with hydroxy-4-proline, and propionic acid with amino acids produced from collagen; hydrolyzed seaweed extracts and related compounds; and hydrolysed vegetable extracts. In a preferred embodiment of the invention, anti-elastase and anti-collagenase agents are Lipacide DPHP and Lipacide C300, both of SEPPIC, France, and Aosaine of SECMA, France.

Free radical scavengers include synthetic pseudopeptides resistant to hydrolysis such as Carcinine HCL; lipoamino acids such as L-lysine lauroylmethionine; plant extracts containing multi-enzymes; and natural tocopherol and related compounds. In a preferred embodiment of the invention, free radical scavengers are Alistin of EXCYMOL, France, Lipacide LML of SEPPIC France and Radiallne® of COLETICA, France.

Seboregulators include lipoamino acids of natural origin such as capryloyl glycine; oxidative enzyme mixtures; and mixtures of hydrolyzed yeast proteins and vitamins and related compounds. In a preferred embodiment of the invention, seboregulators are Asebiol® BT of LABORATOIRES SEROBIOLOGIQUES, France; Lipacide C8G of SEPPIC, France; Sebomine/SB12 of SEDERMA, France; and Biomeris of BIOPOLE, Belgium. (see Examples 37–41)

Hydratives include hydroxylated aliphatic acids such as tri-hydroxy palmitic acid; seaweed extracts; nectar/honey extracts; lipoamino acids such as lysine PCA (where PCA is an amino acid derived from glutamic acid) and related compounds. In a preferred embodiment of the invention, hydratives are selected from Codiavelane of SECMA, France; Lysidone® of UCDB, France; Hydropectotol SM of SEDERMA, France; and Melhudran® of LABORATORIES SEROBIOLOGIQUES, France.

AHA specific products can be mono-, di-, tri-hydroxy acids of natural origin, which may further be linked to polysaccharides or proteins. In a preferred embodiment of the invention, AHA specific products are Glycacid® and Protacid® of COLETICA, France; Multifruit® BSC of BROOKS INDUSTRIES INC, USA; Amidroxy of ALBAN MULLE INT., France; and AHA extracts of PHYTOCHIM, France Furthermore, the cosmetic pad may contain other additives selected from the group consisting of at least one of an anti-microbial, an anti-irritant, an anti-oxidant, a plasticizer, a preservative and a solubilizer, known in the art to be suitable for topical application.

According to a preferred embodiment, the method of preparation of a typical cosmetic pad provided by the invention includes the following steps:

1. Dissolving the cosmetic agents, plant polar lipids and other additives in a pressure sensitive adhesive polymer by continuous stirring at ambient temperature, to prepare a homogeneous mixture.

2. Coating a thin layer of the mixture onto a polyester film using an appropriate coating device. The system is then dried in an oven at 60° to 75° C. for 15–30 minutes. During plant scale manufacturing, the system is dried through a tunnel under a filtered air stream for a shorter time.

3. Laminating the above system onto a polystyrene film where the multi laminate web is cut to a pad of desired shape and size. The composition of the polymeric matrix is given on a dry basis as percentage of each active over the total weight of the polymeric matrix wherein the active substances and additives were incorporated.

In the preferred embodiment, the composition of a typical pad can comprise at least one of the cosmetic actives from those listed above in an amount of 1 to 20% w/w, together with one or more anti-microbials in an amount of 0 to 5% w/w, or preferably 0.1 to 3% w/w;

one or more anti-oxidants in an amount of 0 to 4% w/w, or preferably 0.1 to 2% w/w;

one or more anti-irritants in an amount of 0 to 7% w/w, or preferably 0.01 to 3% w/w;

one or more solubilizers in an amount of 0 to 15% w/w, or preferably 1 to 10% w/w;

one or more preservatives in an amount of 0 to 10% w/w or preferably 0 to 5%; and at least one of a pressure sensitive adhesive from those listed above in an amount of 70 to 95% w/w.

The present invention is further illustrated by the following examples, which, however are not to be seen as limiting the scope of the invention.

EXAMPLES

Example 1–8

Cosmetic Pads Containing Skin Whitening Agents

A composition of a cosmetic pad containing a skin whitening agent, at specified amounts is described in Table 1.

TABLE 1

Skin-whitening Agent Pad Composition

| COMPONENT | QUANTITY, % w/w (on a dry basis) |
|---|---|
| Ceramide preparation | 0.5 |
| Etioline[1] | 5.0 |
| DL-α-tocopherol | 1.0 |
| Gatuline whitening[2] | 5.0 |
| Ascorbyl palmitate | 2.0 |
| Duro-Tak ® 87-2196 | 86.5 |

[1]Etioline is an African plant extract (Matricarpe of Spermacoccea genus), which can inhibit tyrosinase, an enzyme responsible for melanin synthesis.
[2]Gatuline whitening obtained by fermentation of kojic and lactic acids is a tyrosinase inhibitor.

A method for producing the pad having the above composition was as follows: Ceramide plant preparation (0.5 g), Etioline (5.0 g), DL-α-tocopherol (1.0 g), Gatuline (5.0 g) and ascorbyl palmitate (2.0 g) are added to 272.17 g Duro-Tak 87-2196 (45% of total solids) and the mixture was stirred at ambient temperature until all the ingredients have dissolved. The mixture was allowed to stand for several minutes so as to remove air bubbles.

The adhesive mixture was formulated into a pad (patch) system as follows. Using an appropriate counting device (square tool steel Multi Clearance Applicator sold by BYK Gardner) with a 10 mil casting gap, a layer of adhesive mixture was coated onto a siliconized polyester film and dried in an oven at 60° C. for 15–18 minutes. A low density polyethylene film (CoTran 9720, 3191) was laminated onto the adhesive film. The system was delaminated and relaminated on the top of the siliconized side of polystyrene film (REXAM Release) of 10 mil thickness. The final thickness of the dried polymeric matrix was 2 to 3 mils.

The multi-layer laminate was then cut to form a pad of circular shape with nominal size of 1.33 cm² and thickness of 10 to 16 mils.

Similar to the above formulation, additional compositions of a cosmetic pad containing skin whitening agents are presented in Table 2 (the quantities are given as % w/w, on a dry basis).

TABLE 2

Additional Skin-whitening Agent Pad Compositions

| COMPONENT | Ex. 2 | Ex. 3 | Ex. 4 | Ex. 5 | Ex. 6 | Ex. 7 | Ex. 8 |
|---|---|---|---|---|---|---|---|
| Melawhite[1] | 5 | | 2 | | | | |
| Ascorbosilane C | 5 | 3 | 3 | | | 5 | |
| Kojic acid | 1 | 2 | 2 | | 5 | 5 | 3 |
| Ceramide preparation | 1 | 1 | 1 | 1 | 1 | 1 | 1 |
| Arbossa[2] | | 6 | | | | | |
| Ascorbyl palmitate | | | 2 | 2 | 2 | 3 | |
| Etioline[3] | | | | 5 | 5 | | |
| Gatuline whitening[4] | | | | | 5 | | |
| Lactic acid | | | | 2 | | | |
| Vitamin C | | | | | 2 | | |
| Biowhite ™[5] | | | | | | | 5 |
| DL-a-tocopherol | 1 | 1 | 1 | 1 | 1 | 1 | 1 |
| Polymeric[6] adhesive matrix | 87 | 87 | 84 | 84 | 89 | 85 | 90 |

[1]Melawhite is a peptide mixture with anti-tyrosinase activity.
[2]Arbossa is a plant extract containing flavonoids, arbutin, phenolic acid, ascorbic acid.
[3]Etioline is an African plant extract (Matricarpe of Spermacoccea genus), which can inhibit tyrosinase, an enzyme responsible for melanin synthesis.
[4]Gatuline whitening obtained by fermentation, of kojic and lactic acids is a tyrosinase inhibitor.
[5]Biowhite ™ is a plant extract containing triterprenoides, phenylflavones, tannins, etc.
[6]The polymeric adhesive matrix can be made of a single adhesive or a mixture of adhesives.

Examples 9–11

Cosmetic Pads Containing Anti-blotching Agents

Compositions of a cosmetic pad containing anti-blotching agents are given in the Table 3 (the quantities are presented as % w/w, on a dry basis). The manufacturing procedure follows the same steps described in Example 1.

TABLE 3

Anti-blotching Agent Pad Compositions

| COMPONENT | Ex. 9 | Ex. 10 | Ex. 11 |
|---|---|---|---|
| Gatuline A[1] | 8 | 5 | |
| Lactic Acid | 1 | 1.5 | 2 |
| Ivy-Phytelenes[2] | | 5 | |
| Bioflavonoids | | 0.5 | 1 |
| Vitamin C | 1 | 1 | 1 |
| ceramide preparation | 1 | 1 | 1 |
| DL-α-tocopheral | 1 | 1 | 1 |
| Polymeric[3] adhesive matrix | 88 | 85 | 94 |

[1]Gatuline A is a plant extract rich in saponins.
[2]Ivy-Phytelenes is a hydroglycolic plant extract containing flavonoids, caffeic acid, chlorogenic acid, etc.
[3]The polymeric adhesive matrix can be made of a single adhesive or mixture of adhesives.

Examples 12–16

Cosmetic Pads Containing Eye-contour Agents

Compositions of a cosmetic pad containing eye-contour agents are given in Table 4 (the quantities are presented as % w/w, on a dry basis). The manufacturing procedure follows the same steps described in Example 1.

TABLE 4

Eye-contour Agent Pad Compositions

| COMPONENT | Ex. 12 | Ex. 13 | Ex. 14 | Ex. 15 | Ex. 16 |
|---|---|---|---|---|---|
| Esculoside[1] | 1 | | 1 | 1 | 1 |
| Ceramide preparation | 1 | 1 | 1 | 1 | 1 |
| DL-α-tocopherol | 2 | 1 | 2 | 1 | 1 |
| Ascorbyl palmitate | 2 | | | | |
| Lactic acid | | 1 | | 2 | 2 |
| Ascorbosilane C | | 5 | 5 | | |
| Bioflavonoids | | 0.5 | | | |
| Gatuline lifting[2] | | | 6 | | |
| Gatuline RC[3] | | | 4 | | |

TABLE 4-continued

Eye-contour Agent Pad Compositions

| COMPONENT | Ex. 12 | Ex. 13 | Ex. 14 | Ex. 15 | Ex. 16 |
|---|---|---|---|---|---|
| Etioline[4] | | | | 5 | 5 |
| Polymeric[5] Adhesive matrix | 94 | 91.5 | 81 | 90 | 90 |

[1]Esculoside is a flavonoid extract from horse chestnut tree.
[2]Gatuline lifting is a plant extract containing flavanoids, tannins and protein fraction having similar properties to bovine serum albumin.
[3]Gatuline RC is a Beech tree buds extract containing flavonoids, peptides such a phytostimulins and others.
[4]Etioline is an African plant extract (Matricarpe of Spermacoccea genus), which can inhibit tyrosinase, an enzyme responsible for melanin synthesis.
[5]The polymeric adhesive matrix can be made of a single adhesive or a mixture of adhesives.

Example 17

Cosmetic Pads Containing Skin Forming Agents

A composition of the pad containing skin firming agents, at specified amounts is described in Table 5.

The manufacturing procedure is similar to that described in the Example 1 with the exception of using a casting applicator gap of 5 mils and a polystyrene film as removable layer. The thickness of the dry polymeric matrix thus obtained is approximately 1.5 mils. The multi-layer laminate was then cut to form a pad of "eye-shape", or "banana shape" with a thickness of 12 to 15 mils.

TABLE 5

Skin-firming Agent Pad Composition

| COMPONENT | QUANTITY, % w/w (on a dry basis) |
|---|---|
| Gatuline lifting[1] | 3.0 |
| Retinyl palmitate | 2.0 |
| Ceramide preparation | 0.5 |
| DL-α-tocopherol | 0.17 |
| Gatuline RC[2] | 5.0 |
| Gelva 737 | 89.33 |

[1]Gatuline lifting is a plant extract containing flavonoids, tannins and a protein fraction having similar properties to bovine serum albumin.
[2]Gatuline RC is a beech tree buds extract containing flavonoids, peptides such as phytostimulins and others.

Examples 18–19

Cosmetic Pads Containing Natural Bactericide and Fungicide

A composition of the pad containing natural bactericide and fungicide, at specified amounts, is described in Table 6. The manufacturing procedure is similar to that described in Example 1.

TABLE 6

Natural Anti-microbial Agent Pad Compositions

| COMPONENT | Example 18 | Example 19 |
|---|---|---|
| Usnic acid* | 0.5 | 0.1 |
| Irgasan DP 300 | 0.3 | 0.3 |
| Ceramide preparation | 0.5 | 0.5 |

TABLE 6-continued

Natural Anti-microbial Agent Pad Compositions

| COMPONENT | Example 18 | Example 19 |
|---|---|---|
| α-Bisabolol | 1.0 | 1.0 |
| Duro-Tak ® 87-2196 | 97.7 | 98.1 |

*antibacterial agent found in *Usnea barbata*

Example 20

Cosmetic Pads Containing Anti-hyperpigmentation Agent

A composition of the pad containing anti-hyper pigmentation agent, at specified amounts, is described in Table 7.

TABLE 7

Anti-hyperpigmentation Agent Pad Composition

| COMPONENT | QUANTITY % w/w (on a dry basis) |
|---|---|
| Ascorbyl palmitate | 0.10 |
| Oleyl lactate | 2.00 |
| Leucocyanidine | 0.01 |
| Ceramide preparation | 0.50 |
| DL-α-tocopherol | 0.50 |
| Duro-Tak ® 87-2196 | 96.89 |

The manufacturing procedure is similar to that described in the Example 1 with the exception of using a casting applicator gap of 5 mils and a drying temperature of 70–75° C.

Examples 21–22

Cosmetic Pads for Treating Hyperpigmentation

A composition of a pad containing anti-hyperpigmentation agents in specified amounts (% w/w on a dry basis) is given in Table 8. The manufacturing procedure is similar to that described in the Example 1.

TABLE 8

Anti-hyperpigmentation Agent Pad Compositions

| | COMPOSITION, % w/w on a dry basis | |
|---|---|---|
| COMPONENT | Example 21 | Example 22 |
| Arbutine[1] | 0.50 | |
| Hydroquinone | | 2.20 |
| Kojic acid | 2.00 | 2.00 |
| Montane 80 VGA[2] | 5.00 | 5.00 |
| Oxynex 2004[3] | 0.10 | 0.10 |
| Na-disulphite | 0.10 | 0.10 |
| dl-α-tocopherol | 1.00 | 1.00 |
| Ceramide preparation | 1.00 | 1.00 |
| PEG400 | 8.00 | 8.00 |
| α-bisabolol | 1.00 | 1.00 |
| Duro-Tak 87-2353 | 81.30 | 79.60 |

[1]Arbutine is a naturally occurring glucoside of hydroquinone.
[2]Montane 80 VGA is sorbitan monooleate of vegetable source.
[3]Oxynex 2004 is a mixture of citric acid ascorbyl palmitate and butylhydroxy toluene.

Examples 23–25

Cosmetic Pads Containing Slimming/Anti-cellulite Agents

A composition of the pad containing slimming/anti-cellulite agents at specified amounts, is described in Table 9. The manufacturing procedure is similar to that described in Example 1 with exceptions of using drying temperature at 65–70° C. and a removable layer is made of a siliconized polyester film which is overlapped.

Similarly to the above, the following pads were prepared as given in Table 10.

TABLE 9

Anti-cellulite Agent Pad Composition

| COMPONENT | QUANTITY, % w/w (on a dry basis) |
|---|---|
| Bladder-wrack extract (Fucus) | 5.0 |
| Hydrocotyl extract (Centella asiatica) | 3.5 |
| Gingko extract | 1.5 |
| Ceramide preparation | 1.0 |
| Arlacel 80 | 2.0 |
| Duro-Tak ® 87-2196 | 87.0 |

TABLE 10

Anti-cellulite Agent Pad Compositions

| COMPONENT | Ex. 24 | Ex. 25 |
|---|---|---|
| Theophylosilane C | 6 | |
| Ivy glycolic extract | 5 | |
| Fucus extract | 5 | |
| Ceramide preparation | 1 | 1 |
| DL-α-tocopherol | 1 | |
| Red seaweed extract | | 10 |
| Caffeic acid | | 1 |
| Tocopherol nicotinate | | 2 |
| Transcutol | 2 | 2 |
| Polymeric adhesive matrix[1] | 80 | 84 |

[1]The polymeric adhesive matrix can be made of a single adhesive or a mixture of adhesives.

Examples 26–34

Cosmetic Pads Containing Anti-wrinkle Agents

A composition of the pad containing anti-wrinkle agents, at specified amounts, is described in Table 11. The manufacturing procedure is similar to that described in Example 1 with the exception of using a siliconized polyester film of 3 mil thickness and a drying temperature of 70° C.

TABLE 11

Anti-wrinkle Agent Pad Composition

| COMPONENT | QUANTITY, % w/w (on a dry basis) |
|---|---|
| Ceramide preparation | 0.5 |
| Retinyl palmitate | 2.0 |
| DL-α-tocopherol | 0.5 |
| Duro-Tak ® 87-2196 | 97.0 |

TABLE 12

Anti-wrinkle Agent Pad Compositions

| COMPONENT | Ex. 27 | Ex. 28 | Ex. 29 | Ex. 30 | Ex. 31 |
|---|---|---|---|---|---|
| Lactic acid | 3 | | | | |
| Retinyl palmitate | 2 | | | | |
| α-bisabolol | 1 | | | | |
| Ceramide preparation | 1 | 1 | 1 | 1 | 1 |
| Glycerol | 5 | | | | |
| DL-α-tocopheral | 1 | 0.5 | 0.5 | 0.5 | 0.5 |
| Retinoic acid | | 0.1 | 0.025 | 0.01 | 0.1 |
| Linoleic acid | | 5 | 5 | 5 | |
| Irgasan DP 300 | | 0.3 | 0.3 | 0.3 | 0.3 |
| Polymeric[1] adhesive matrix | 87 | 93.1 | 93.175 | 93.19 | 98.1 |

[1]The polymeric adhesive matrix can be made of a single adhesive or a mixture of adhesives.

TABLE 13

Anti-wrinkle Agent Pad Compositions

| Component | Ex. 32 | Ex. 33 |
|---|---|---|
| lactic acid | 5.0 | 5.0 |
| ceramide preparation | 0.5 | 0.5 |
| ATBC[1] | 10.0 | |
| kgasan DP 300 | 0.3 | 0.3 |
| α-bisabolol | 1.0 | 1.0 |
| DL-α-Tocopherol | 0.5 | 0.5 |
| Polymeric[2] adhesive matrix | 82.7 | 92.7 |

[1]ATBC is acetyl tributyl citrate used as a plasticizer.
[2]The polymeric adhesive matrix can be made of a single or mixture of adhesives.

Additional cosmetic pads containing anti-wrinkle agents are given in Tables 11 and 12. (The quantities are expressed as % w/w).

Examples 34–36

Anti-wrinkle Composition

A composition of a pad containing an anti-wrinkle composition at specified amounts is given in Table 14.

The manufacturing of the pad may be achieved according to Example 1 substituting the concentrations of reagents as provided below where they differ from Example 1. Alternatively, the reagents described below may be utilized to form a pad according to manufacturing techniques known in the art.

TABLE 14

Anti-wrinkle Agent Pad Compositions

| Component | Ex. 34 | Ex. 35 | Ex. 36 |
|---|---|---|---|
| Ascorbyl palmitate | 3.0 | 10.0 | 3.0 |
| Lactic acid | 0.5 | 0.5 | 0.5 |
| Retinyl palmitate | 0.1 | 0.1 | 0.1 |
| Ceramide preparation | 0.3 | 0.3 | 0.3 |
| DuroTak ®87-2353 | 96.1 | 89.1 | |
| DuroTak ®87-2510 | | | 96.1 |

Examples 37–40

Cosmetic Pads Containing Seboregulators

A composition of a pad containing a seboregulator at specific amounts (1% w/w on a dry basis) is given in Table 15. The manufacturing procedure is similar to that described in Example 1.

TABLE 15

| Component | Ex. 37 | Ex. 38 | Ex. 39 | Ex. 40 |
|---|---|---|---|---|
| Natrasorb | 27.78 | 16.13 | 25.42 | 16.13 |
| Tween 80 | | | 8.50 | 9.70 |
| Ceramide preparation | 0.50 | 0.50 | 0.50 | 0.50 |
| Polymeric adhesive matrix | 71.72 | 83.37 | 65.58 | 74.67 |

Example 41

Depigmentation of Skin After the Application of Cosmetic Pads on a Preserved Skin Model The aim of this study was to demonstrate the depigmentation efficacy of the pads described in Examples 21 and 22. Human skin was obtained by plastic surgery. The skin was classified as dark photo-type (III or IV). The skin fragments (cutaneous surface equal to 1 cm$^2$) were maintained in a viable state ex vivo in organ culture. The fragments were placed into inserts which were positioned in suspension over a culture cavity and preserved for a period of 21 days in culture medium (the culture medium being renewed 3 times per week). The samples were as follows:

(a) Positive control: Lotion containing 2% hydroquinone (Lierac ®)

(b) Pads containing hydroquinone and kojic acid (Example 22)

(c) Pads containing a stable synthetic hydroquinone derivative (arbutine) and kojic acid (Example 21)

(d) Negative control-untreated skin

Where pads were utilized, a final concentration of 0.04 mg of hydroquinone or arbutine was delivered to each of the sample skin fragments per day for 5 days per week over a period of 21 days. The pigmentation of the skin was evaluated in 300 basal layer cells per skin fragment which were classified histologically before and after treatment by optical microscopy using standard dye techniques. The depigmentation capacity of the pad treated skin refers to the estimate of melanin pigment in the melanocytes and the adjacent keratinocytes in treated samples compared with negative controls.

| Score | Cell characteristics |
|---|---|
| 0–+ | non-pigmented cells or cells showing a few particles, cells having a vacuolated appearance |
| ++ | cells showing a moderate amount of melanin (sparse melanin particles, non-homogeneous) |
| +++ | cells showing a substantial amount of melanin (homogeneous deposit covering more than half of the cytoplasm of the cells. |

The Table below shows the average of the results obtained on 4 skin fragments of prototype III and IV, expressed as the percentage of cells for each pigmentation score.

| | score 0–+ | score++ | score+++ |
|---|---|---|---|
| control skin | 5.3 ± 1.85% | 56.6% ± 6.1% | 38.25 ± 5.7% |
| skin and pad 1 | 9.9 ± 4.0% | 65.7 ± 2.9% | 24.4 ± 4.9% |
| skin and pad 2 | 13.2 ± 4.5% | 69.2 ± 2.3% | 17.55 ± 2.3% |
| skin and LIERAC® | 11.5 ± 6.2% | 66.5 ± 2.3% | 21.95 ± 5.1% |

The results show that the highly pigmented cells (+++) decreased in the presence of pad 1, 2 and the lotion with the maximum effect seen for pad 2 (with arbutine). Associated with a decrease in highly pigmented cells, an increase of slightly pigmented cells (++) was observed for treated and untreated skin. The pads exhibit a depigmentation effect similar to the reference cream. However, the pad offers the advantage of direct application to the target site leaving the healthy skin unaffected by the active ingredients.

The treatment of hyperpigmentation with ointments or lotions commonly requires applications extending over 5 to 6 months. The experiments shown above in which treatment occurred over 21 days shows a significant effect on reducing hyperpigmentation using pads, the effect being at least that of the positive control but with the advantage of precise targeting of active agent to the site for treatment.

I claim:

1. A device for the improvement of skin appearance, comprising: a pad having a backing layer, a release layer, and a vehicle located therebetween, the vehicle comprising a cosmetic formulation and a skin permeation enhancer, wherein the skin permeation enhancer includes a plant polar lipid.

2. A device according to claim 1, wherein the plant polar lipid comprises a ceramide preparation containing at least one of a ceramide or glycoceramide.

3. The device according to claim 1, wherein the cosmetic formulation comprises a cosmetic active agent and at least one of an antimicrobial agent, an antioxidant, a preservative, an anti-irritant, a plasticizer and a solubilizer.

4. The device according to claim 2, wherein the cosmetic formulation further comprises a cosmetic active agent and at least one of an anti-microbial agent, an anti-oxidant, a preservative, an anti-irritant, a plasticizer and a solubilizer.

5. The device according to claim 1, wherein the concentration range of the plant polar lipid is 0.1 to 5%w/w.

6. The device according to claim 2, wherein the concentration range of the plant polar lipid is 0.1 to 5%w/w.

7. The device according to claim 3, wherein the concentration range of the cosmetic active agent is 1 to 20% w/w, the microbial agent is 0 to 5% w/w, the antioxidant is 0 to 4% w/w, the preservative is 0 to 5% w/w, the anti-irritant is 0 to 7% w/w, the plasticizer is 0–10% w/w and the solubilizer is 0 to 5% w/w.

8. The device according to claim 3, wherein the cosmetic agent is selected from the group consisting of anti-hyperpigmentation agents, anti-blotching agents, anti-aging agents, eye contour agents, slimming agents, anti-cellulite agents, soothing agents, sunburn agents, anti-irritating agents, skin firming agents, anti-elastase agents, anti-collagenase substances, free radical scavengers, seboregulators, hydratives, and α-hydroxy acids, vitamins, anti-oxidants and minerals.

9. A method of delivering a cosmetic agent to a topical site for improving skin appearance, comprising:

(a) selecting a multilaminate device comprising a backing layer, a vehicle and a release liner;

(b) providing the cosmetic agent and an enhancer for dispersion within the vehicle wherein the enhancer is a sphingolipid; and (c) forming a device for improvement of skin appearance.

10. A method according to claim 9, wherein the sphingolipid is a plant polar lipid.

11. A method according to claim 10, wherein the plant polar lipid is a ceramide preparation containing at least one of a glycoceramide or a ceramide.

12. A method according to claim 9, wherein improving skin appearance further includes any of increasing skin elasticity, decreasing wrinkles, removing pimples, reducing cellulitis, increasing skin moisture, regulating sebum secretion and reducing hyperpigmentation and blotching.

13. A composition for enhancing the penetration of agents through the outer layer of the skin, comprising:

a preparation of plant polar lipid, the plant polar lipid containing at least one of a ceramide and a glycoceramide.

14. A method of improving skin appearance, comprising:
  (a) removing the release layer on the device of claim 1 to expose the vehicle; and,
  (b) contacting the vehicle to skin.

15. The method of claim 14 wherein improving skin appearance comprises increasing skin moisture.

16. The method of claim 14 wherein improving skin appearance comprises regulating sebum secretion.

17. The method of claim 14, wherein improving skin appearance comprises reducing hyperpigmentation or blotching.

18. The method of claim 14, wherein improving skin appearance comprises increasing skin elasticity.

19. The method of claim 14, wherein improving skin appearance comprises decreasing wrinkles.

20. The method of claim 14, wherein improving skin appearance comprises reduction in cellulitis.

* * * * *